United States Patent
Reger et al.

(10) Patent No.: US 10,883,260 B2
(45) Date of Patent: Jan. 5, 2021

(54) SCENT BARRIER AND DISPENSER

(71) Applicants: Andrew Lee Reger, Fort Wayne, IN (US); Donald Dickman, Leo, IN (US)

(72) Inventors: Andrew Lee Reger, Fort Wayne, IN (US); Donald Dickman, Leo, IN (US)

( * ) Notice: Subject to any disclaimer, the term of this patent is extended or adjusted under 35 U.S.C. 154(b) by 94 days.

(21) Appl. No.: 16/201,531

(22) Filed: Nov. 27, 2018

(65) Prior Publication Data

US 2019/0218761 A1 Jul. 18, 2019

Related U.S. Application Data

(60) Provisional application No. 62/618,294, filed on Jan. 17, 2018.

(51) Int. Cl.
| | | |
|---|---|---|
| E03D 9/00 | (2006.01) | |
| E03D 9/03 | (2006.01) | |
| A61L 9/05 | (2006.01) | |

(52) U.S. Cl.
CPC .............. E03D 9/005 (2013.01); A61L 9/05 (2013.01); E03D 9/032 (2013.01)

(58) Field of Classification Search
CPC ............ E03D 9/005; E03D 9/032; A61L 9/05
See application file for complete search history.

(56) References Cited

U.S. PATENT DOCUMENTS

| | | | |
|---|---|---|---|
| 5,307,525 A | 5/1994 | OBrien | |
| 5,958,334 A | 9/1999 | Haddon | |
| 6,029,286 A | 2/2000 | Funk | |
| 6,817,040 B2 | 11/2004 | Klinkhammer et al. | |
| 7,316,038 B2 | 1/2008 | Egeresi | |
| 7,788,740 B2 | 9/2010 | De Belder et al. | |
| 7,832,025 B2 | 11/2010 | Virica et al. | |
| 8,603,257 B2 | 12/2013 | Burt et al. | |
| 8,664,172 B2 | 3/2014 | Veltman et al. | |
| 8,966,674 B2 | 3/2015 | Lu et al. | |
| 9,546,477 B2 | 1/2017 | Butter-Jentsch et al. | |
| 9,724,445 B2 | 8/2017 | Rabin et al. | |
| 2002/0086039 A1* | 7/2002 | Lee | C03C 3/097 424/401 |
| 2005/0142084 A1* | 6/2005 | Ganguly | A61K 8/26 424/63 |
| 2008/0313795 A1 | 12/2008 | Lu | |
| 2010/0299818 A1 | 12/2010 | Lu | |
| 2013/0104304 A1 | 5/2013 | Wilson et al. | |
| 2014/0120039 A1* | 5/2014 | Graham | A61K 8/365 424/44 |
| 2014/0255077 A1* | 9/2014 | Mobarak | A61K 8/732 401/88 |
| 2017/0106333 A1* | 4/2017 | Zhu | B01D 53/1406 |
| 2018/0155910 A1 | 6/2018 | Reichert et al. | |
| 2018/0223517 A1 | 8/2018 | Wood et al. | |
| 2019/0365634 A1* | 12/2019 | Boyle | A61Q 19/10 |
| 2020/0016216 A1* | 1/2020 | Whitlock | A61P 25/08 |

* cited by examiner

Primary Examiner — J C Jacyna
(74) Attorney, Agent, or Firm — Dunlap Bennett & Ludwig, PLLC; Brendan E. Squire

(57) ABSTRACT

A rim-mounted toilet insert that creates a scented oil barrier to automatically trap odors between each flush. The apparatus and composition blocks toilet odors automatically, so users don't have to remember to apply it before you use the restroom.

11 Claims, 2 Drawing Sheets

SCENT BARRIER AND DISPENSER

CROSS-REFERENCE TO RELATED APPLICATION

This application claims the benefit of priority of U.S. provisional application No. 62/618,294, filed Jan. 17, 2018, the contents of which are herein incorporated by reference.

BACKGROUND OF THE INVENTION

The present invention relates to bathroom odor control, and more particularly to the control of undesirable scents in the bathroom.

A recurring problem that the present invention solves is preventing embarrassing bathroom odors after someone defecates.

While other odor barriers, such as oils exist, the problem with other devices is the user has to remember to apply the odor barrier before they go. The user also has to get close to the water with their bare hand to apply the odor barrier oil.

Cost is another important consideration. For example, an 8 oz. bottle of the leading toilet spray costs almost $20. Many people tend to overuse the sprays in order to "be safe." In addition, when you're in a hurry, people tend to forget to apply the coating beforehand.

As can be seen, there is a need for an apparatus and method for automatically dispensing an odor barrier.

SUMMARY OF THE INVENTION

In one aspect of the present invention, an apparatus for dispersing a scent barrier to a water level carried in a toilet bowl, is disclosed. The apparatus includes a clip dimensioned to secure to a rim of a toilet bowl. A basket is suspended below the dip. A top opening of the basket is positioned to receive a water flow delivered through an outlet defined beneath and around a periphery of the rim of the toilet bowl when secured to the rim of the toilet bowl. The basket has a plurality of apertures defined through a surface of the basket. A cartridge is dimensioned to be received within the basket wherein the cartridge contains an odor barrier material.

In some embodiments, the cartridge is formed of a composition comprising: baking soda, corn starch, an oil, and glycerin. The cartridge may also include a fragrance. The composition may include between about 20%-30% baking soda; between about 40%-60% corn starch; between about 20%-30% oil; and between about 5-6% glycerin. The fragrance may be an essential oil.

In a preferred embodiment, the composition is between about 23%-34% baking soda; between about 41%-56% corn starch; between about 20%-31% oil; and between about 3.2% and 6.2% glycerin. The composition may further include about 1.5% and 4.1% of an essential oil.

In other aspects of the invention, a composition of matter providing slow release of an odor barrier is disclosed. In some embodiments, the composition of matter includes: between about 20%-30% baking soda; between about 40%-60% corn starch; between about 20%-30% oil; and between about 5%-8% glycerin. The composition may also include a fragrance. The fragrance is about 2%-3% of an essential oil.

In a preferred embodiment, the composition includes: between about 23%-34% baking soda; between about 41%-56% corn starch; between about 20%-31% oil; and about 3.2% and 6.2% glycerin. The composition may also include a fragrance. The fragrance may be about 1.5% and 4.1% of an essential oil.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention provide an improved odor barrier dispersant product and a carrier for automatically applying an odor barrier in a toilet bowl.

Figure 1:
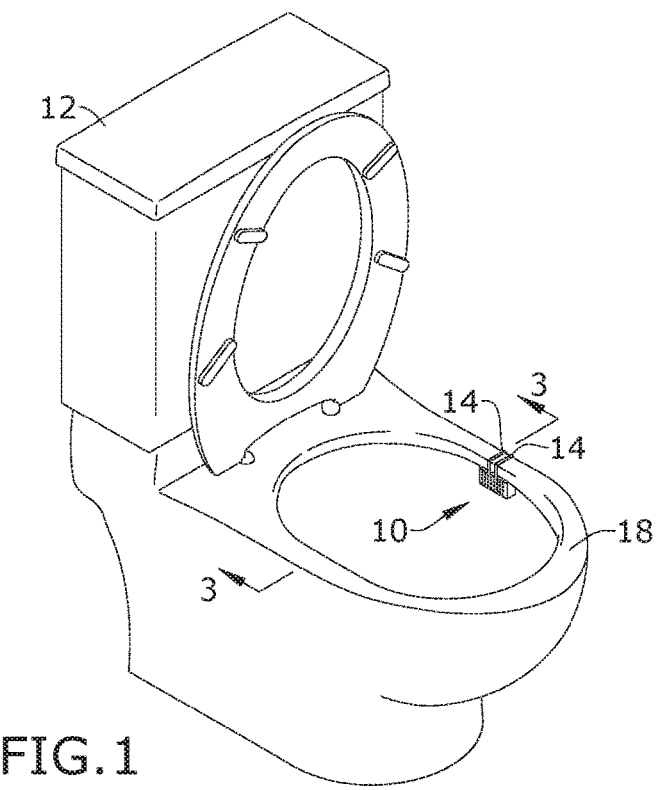
FIG. 1 is a perspective view of the rim mounted toilet insert for dispersing a scent barrier.
Figure 2:
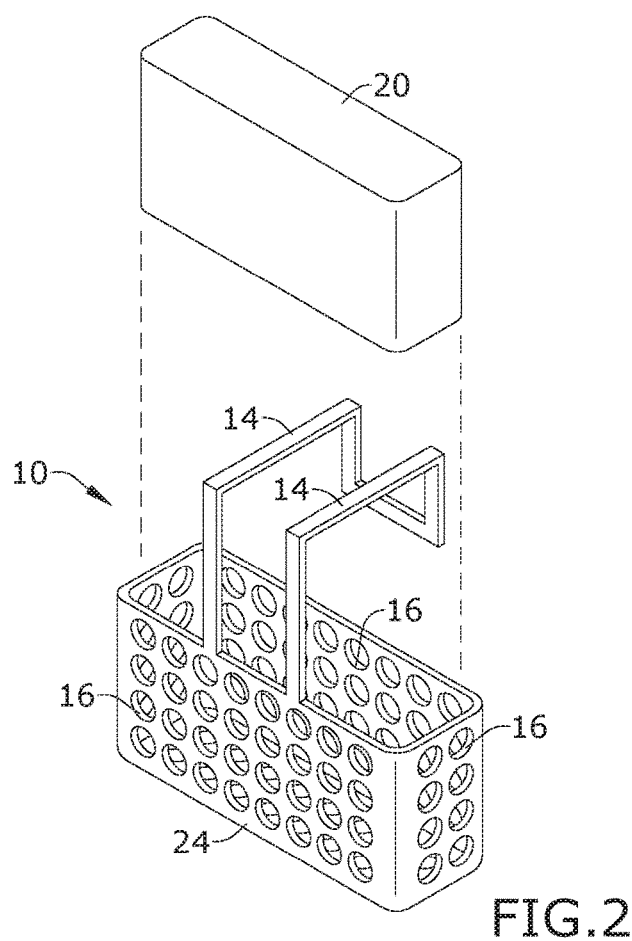
FIG. 2 is an exploded view of the rim mounted toilet insert and dispersant carrier.

As seen in reference to FIGS. 1 and 2, the rim mounted toilet bowl carrier 10 includes is mounted to a toilet bowl 12 via a clip 14 that attaches the carrier 10 to a rim 18 of the toilet bowl 12. The carrier 10 includes a basket 24 that is suspended below the clip 14 and in abutment with a sidewall of the interior of the toilet bowl 12. The basket 24 has a plurality of apertures 16 defined about the periphery of the basket 24. The basket 24 is dimensioned to carry a cartridge 20 containing an odor barrier material, such as an oil. The cartridge 20 containing the odor barrier material may also include a fragrance that is dispersed along with the odor barrier material.

Figure 3:
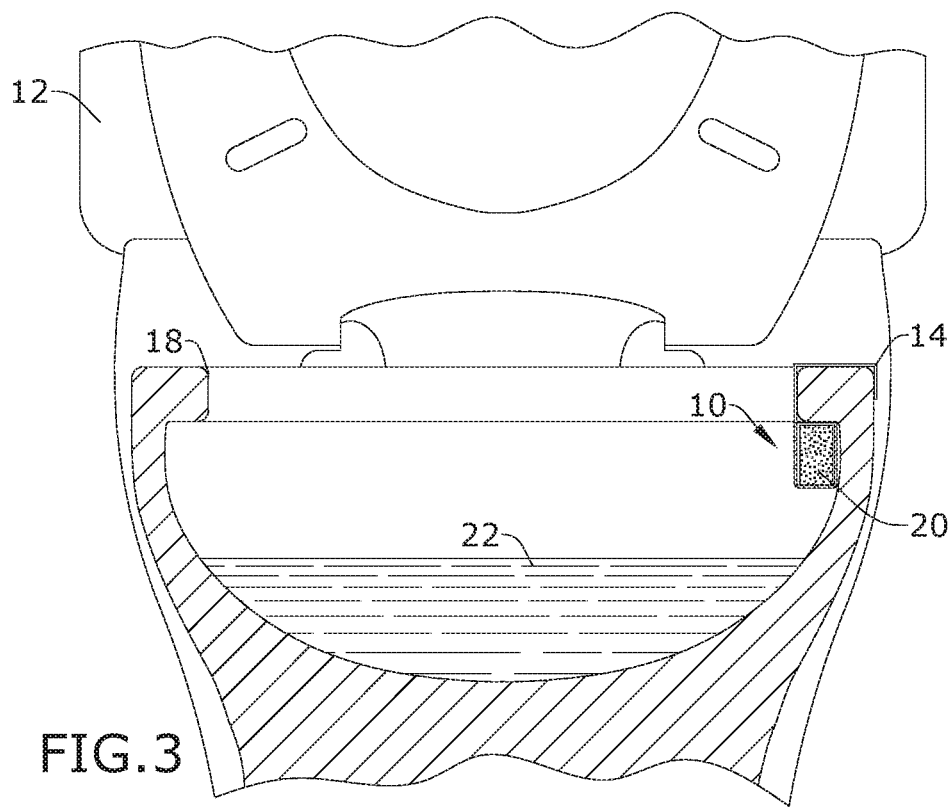
FIG. 3 is a sectional view of the rim mounted toilet insert taken along line 3-3 of FIG. 1.
Figure 4:
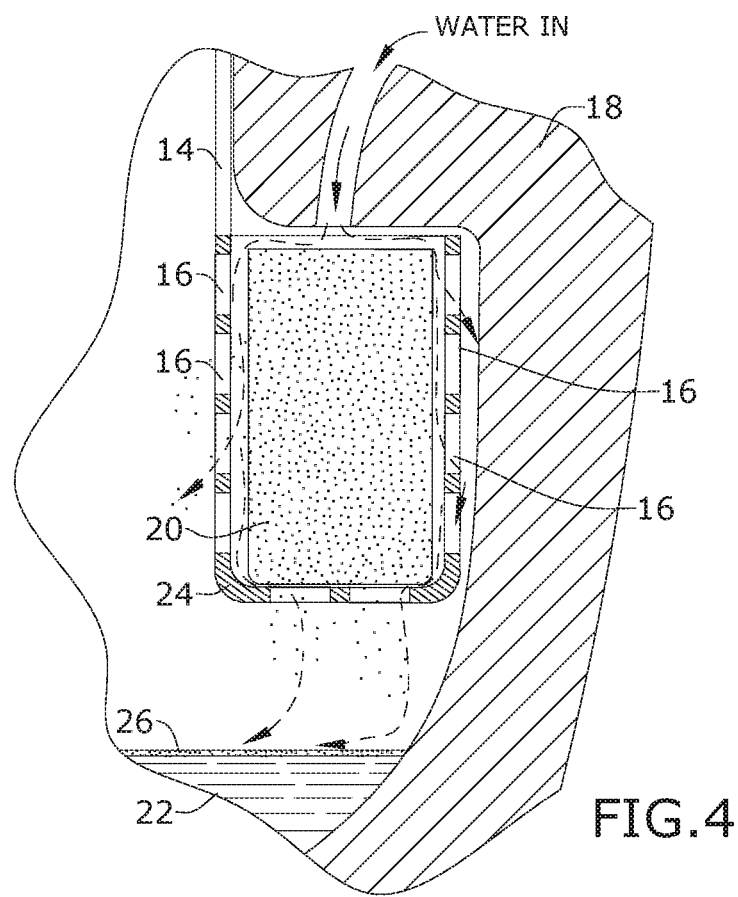
FIG. 4 is a detail sectional view of the rim mounted toilet insert and dispersant carrier.

As seen in reference to FIGS. 3 and 4, the carrier 10 is positioned such that the cartridge 20 is suspended in an elevated position above a water level 22 within the toilet bowl. The carrier 10 positions a top opening of the basket 24 proximal to a water delivery outlet defined beneath and around the periphery of the toilet bowl rim 18. When the toilet 12 is flushed, water 22 carried through the water delivery outlet is directed over the cartridge 20.

As the water 22 flows over the cartridge 20 and through the plurality of apertures 16 defined in the basket 24. The odor barrier material is gradually released from the cartridge 20 and entrained with the water 22 for dispersal as an odor barrier film 26 atop the water level 22. Following a bowel movement, the odor barrier material temporarily disperses, then returns to provide the odor barrier film 26 over the water surface 22, containing the offensive odors beneath the odor barrier film 26.

The cartridge 20 includes a composition formed from baking soda, corn starch, an oil, and glycerin. Optionally, a fragrance may be included, which may also be an essential oil fragrance. In some embodiments, the cartridge composition 20 may be formed with between about 20%-30% baking soda; between about 40%-60% corn starch; between about 20%-30% oil; between about 5% and 6% glycerin; and optionally, between about 1.5% and 4.1% essential oil.

In a preferred embodiment, the cartridge composition 20 is formed with between about 23%-34% baking soda; between about 41%-56% corn starch; between about 20%-31% oil; between about 32% and 6.2% glycerin, and optionally, between about 1.5% and 4.1% essential oil. More preferably, the cartridge composition 20 is formed with 22.9% baking soda, 45.7% corn starch, 22.9% oil, 5.7% glycerin, and 2.8% of an essential oil.

The foregoing composition is mixed and formed into the cartridge 20 which is conveniently contained and readily replaceable within the carrier basket 24. The composition has been discovered to provide an ideal water soluble dispersant for delivering a suitable quantity of odor blocking oil. The composition provides a time release medium that lasts for an extended period, typically on the order of about 70 flushes. The cartridge 20 may then be conveniently be replaced as needed. Optionally, the basket 24 may be enclosed, with apertures 16 to receive the water flow through the carrier 10, and the entire unit disposed of when the cartridge 20 is depleted.

It should be understood, of course, that the foregoing relates to exemplary embodiments of the invention and that modifications may be made without departing from the spirit and scope of the invention as set forth in the following claims.

What is claimed is:

1. An apparatus for dispersing a scent barrier to a water level carried in a toilet bowl, comprising:
    a clip dimensioned to secure to a rim of a toilet bowl;
    a basket suspended below the clip, a top opening of the basket positioned to receive a water flow delivered through an outlet defined beneath and around a periphery of the rim of the toilet bowl when secured to the rim of the toilet bowl, and a plurality of apertures defined through a surface of the basket; and
    a cartridge dimensioned to be received within the basket, wherein the cartridge is formed of a composition of 20%-30% baking soda; 40%-60% corn starch; 20%-30% oil; and 2-3% glycerin.

2. The apparatus of claim 1, wherein the cartridge further comprises a fragrance.

3. The rim mounted toilet insert of claim 2, wherein the fragrance is an essential oil distinct from the oil.

4. An apparatus for dispersing a scent barrier to a water level carried in a toilet bowl, comprising:
    a clip dimensioned to secure to a rim of a toilet bowl;
    a basket suspended below the clip, a top opening of the basket positioned to receive a water flow delivered through an outlet defined beneath and around a periphery of the rim of the toilet bowl when secured to the rim of the toilet bowl, and a plurality of apertures defined through a surface of the basket; and
    a cartridge dimensioned to be received within the basket, wherein the composition is between about 23%-34% baking soda; between about 41%-56% corn starch; between about 20%-31% oil; and between about 3.2% and 6.2% glycerin.

5. The rim mounted toilet insert of claim 4, further comprising between about 1.5% and 4.1% of an essential oil distinct from the oil.

6. A composition of matter providing slow release of an odor barrier, comprising:
    between about 20%-30% baking soda;
    between about 40%-60% corn starch;
    between about 20%-30% oil; and
    5%-6% glycerin.

7. The composition of claim 6, comprising:
    a fragrance.

8. The composition of claim 7, wherein the fragrance is about 2%-3% of an essential oil distinct from the oil.

9. A composition of matter, comprising:
    between about 23%-34% baking soda;
    between about 41%-56% corn starch;
    between about 20%-31% oil; and
    about 3.2% and 6.2% glycerin.

10. The composition of claim 9, further comprising:
    a fragrance.

11. The composition of claim 10, wherein the fragrance is about 1.5% and 4.1% of an essential oil distinct from the oil.

* * * * *